United States Patent [19]

Dias

[11] Patent Number: 5,152,291

[45] Date of Patent: Oct. 6, 1992

[54] ACOUSTIC FIBER MEASUREMENT OF INTRAVASCULAR BLOOD

[75] Inventor: J. Fleming Dias, Palo Alto, Calif.

[73] Assignee: Hewlett-Packard Company, Palo Alto, Calif.

[21] Appl. No.: 579,428

[22] Filed: Sep. 7, 1990

[51] Int. Cl.$^5$ .............................................. A61B 8/12
[52] U.S. Cl. ......................... 128/661.08; 128/662.06; 73/861.25
[58] Field of Search ....................... 128/660.02, 660.03, 128/662.06, 24 A, 634, 673

[56] References Cited

U.S. PATENT DOCUMENTS

| | | |
|---|---|---|
| 4,270,050 | 5/1981 | Brogardh . |
| 4,431,006 | 2/1984 | Trimmer et al. ............... 128/662.05 |
| 4,587,972 | 5/1986 | Morantte, Jr. ................. 128/660.03 |
| 4,716,363 | 12/1987 | Dukes et al. . |

FOREIGN PATENT DOCUMENTS

| | | |
|---|---|---|
| 0253559A1 | 7/1987 | European Pat. Off. . |
| WO0001269 | 3/1987 | World Int. Prop. O. ...... 128/662.06 |

OTHER PUBLICATIONS

"A Single-Crystal Ultrasonic Catheter-Tip Velocity Probe," Hartley et al., *Medical Instrumentation* (1974), vol. 8, pp. 241-243, No. 4.
"Subselective Measurement of Coronary Blood Flow Velocity Using a Sterrable Doppler Catheter," Silbey et al., *JACC* (Dec. 1986), vol. 8, No. 6.
"Intravascular Ultrasound: Development and Clinical Potential," Yock et al., *American Journal of Cardiac Imaging*, vol. 2, pp. 185-193, No. 3, (Sep. 1988).
"Similarities and Differences Between Fiber Acoustics and Fiber Optics," C. K. Jen, *IEEE 1985 Ultrasonics Symposium*, Oct. 16-18, 1985.
"Review of Intracoronary Doppler Catheters," Craig J. Hartley, *International Journal of Cardiac Imaging* (1989) vol. 4, pp. 159-168.
"Optical Fluorescence and its Application to an Intravascular Blood Gas Monitoring System," Gehrich et al., IEEE (1969), vol. BME-33, No. 2, pp. 117-131.
"Measurements in Medical Practice and Research," Tsitlik et al., Sensors, Jul. 1987, pp. 11-17.
"Fiber-Optic Diaphragm-Curvature Pressure Transducer," Lawson et al., Optical Society of America, vol. 8, No. 5, pp. 286-288.
"Very High Frequency Pulsed Doppler Apparatus", *Ultrasound in Medicine and Biology*, vol. 15, No. 2, 121-131; (1989), M. Berson, F. Patat, Z. Q. Wange, D. Besse and L. Pourcelot.
"Grafted Hydrophilic Polymers as Optical Sensors", *Sensor Technology, Feb. 1, 1988.*
"Measuring Coronary Blood Flow", *Sensor Technology*, Feb. 1988.
*Doppler Ultrasound and Cardiology*, Liv Hatle, M.D., Bjorn Angelsen, Dr. Techn., 1982.
"Synchronized Pulsed Doppler Blood Flow and Ultrasonic Dimension Measurement in Conscious Dogs," *Ultrasound in Medicine and Biology*, vol. 4, pp. 99-110, 1978; C. J. Hartley, H. G. Hanley, R. M. Lewis, and J. S. Cole.
"Pulsed Ultrasonic Doppler Blood-Flow Sensing", Donald W. Baker; *IEEE Transactions on Sonics and Ultrasonics*, vol. 80, SU-17, No. 3, Jul. 1970.
"A New Doppler Flowmeter System and its Operation with Catheter Mounted Transducers," *Cardiovascular Applications of Ultrasound*, Robert S. Reneman, Editor, North-Holland/American Eleseuir Publishers J. M. Reid, D. L. Davis, H. J. Rickets and M. P. Spencer.

*Primary Examiner*—Francis Jaworski

[57] ABSTRACT

One or more acoustic fiber guides are used to carry certain modes of acoustic energy to the tip of a catheter. Using these fibers, reflected sound (Doppler Sound) measurements are made in a blood environment without the risk to the patient associated with the use of an electrical transducer at the distal end of the catheter. Due to the size reduction provided, the Doppler probe is suitable for monitoring the blood flow in the coronary arteries. Using this invention wherein sound is transported to the catheter tip, risk is reduced and the catheter is significantly less expensive, and therefore can be treated as disposable. By the addition of optical fibers tipped with specific dyes and excited by optical energy of appropriate wavelength, the catheter tip system can also be utilized simultaneously as a combined (integral) optical blood gas and pH monitor using optical fluorescence and an acoustic Doppler velocity transducer.

16 Claims, 5 Drawing Sheets

ACOUSTIC FIBER MEASUREMENT OF INTRAVASCULAR BLOOD

INTRODUCTION

1. Technical Field

This invention pertains to catheter devices and more specifically to catheter devices useful for a combined in vivo measurement of blood gas velocity and blood composition.

2. Background of the Invention

Figure 1:
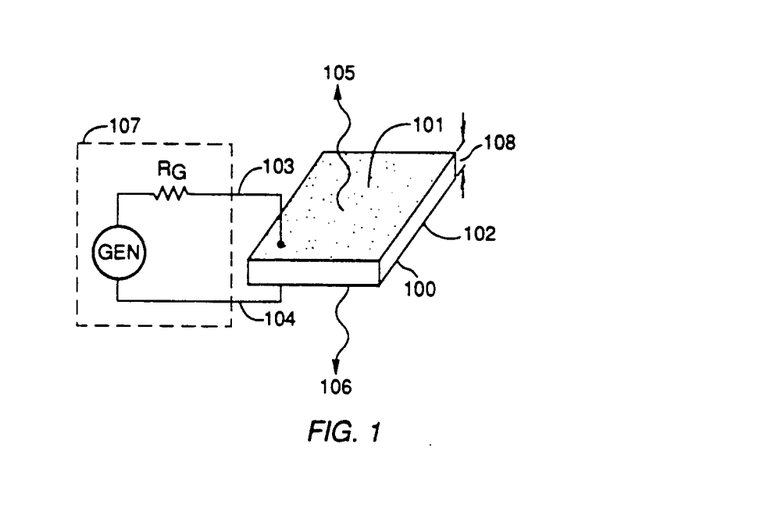
FIG. 1 depicts a typical prior art PZT transducer.

It is known in the prior art how to measure blood velocity utilizing a catheter having a piezoelectric transducer (such as PZT) at its tip. The piezoelectric material is generally lead zirconate titanate which is a type of ceramic. A typical transducer 100 has two active faces 101 and 102, as shown in FIG. 1.

These faces are metallized by vacuum depositing thin films of chromium (200 Å) and gold (2000 Å). Leads 103, 104 are then attached to faces 101, 102, respectively. When connected to a pulse generator 107, transducer 100 converts the electrical signals into acoustic pulses 105, 106. If acoustic pulse 105 is designated as being in the forward direction, the acoustic pulse 106 is either damped (for example, by placing a suitable damping material on face 102 of transducer 100, as is well known in the art), or pulse 106 is forced to be reflected in a forward direction in order to add to the energy provided by forward pulse 105. Pulse 106 is reflected, for example, by adding impedance mismatch, for example, by placing transducer 100 such that face 102 is exposed to the ambient environment. The reverse is also true—i.e. an acoustic pulse impinging on either face 101 or 102 creates an electrical signal on leads 103, 104. Such PZT transducers are generally circular or annular when used at the tip of a catheter. Thickness 108 of transducer 100 determines the operating frequency—at 20 MHz the thickness is about 0.1 mm.

Figure 2:
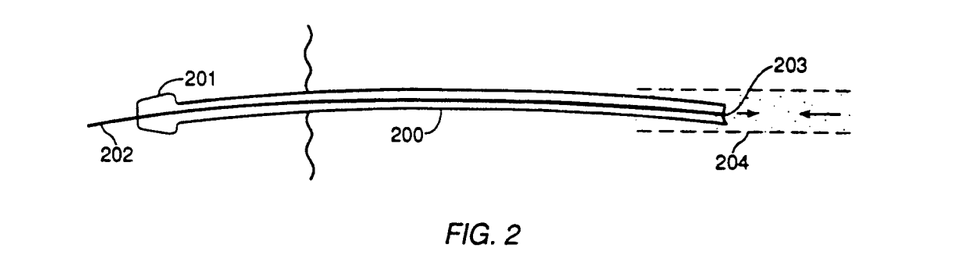
FIG. 2 depicts typical prior art catheter which has been used to insert a PZT sensor into the bloodstream of a patient.

FIG. 2 depicts the use of such a prior art catheter device, including PZT transducer 203 located at its distal end which, as shown in FIG. 2, has been inserted into blood vessel 204. Electrical connection 202 is contained within catheter 200 and serves to connect PZT transducer 203 to external circuitry (not shown) after exiting from proximal end 201 of catheter 200. As sound energy is emitted from PZT transducer 203, sound is reflected by the red blood cells contained within blood vessel 204, thereby causing a received electrical signal to be generated on electrical lead 202, which can then be detected by external circuitry. This detected signal is indicative of blood velocity.

The fabrication of these prior art PZT transducers is difficult and entails a significant amount of labor. While the use of higher frequencies results in a better signal to noise ratio, using such prior art transducers at higher frequencies presents a size problem, because the thickness scales downwards. At higher frequencies, such prior art PZT transducers are, for all practical purposes, impossible to manufacture economically. For example, at 40 MHz, the transducer thickness would be about 2 mils (0.05 mm). Moreover, there is always a risk to the patient at all frequencies because of the existence of an electrical potential at the distal end of the catheter, which introduces the risk of fibrillation, particularly when measuring blood flow near the coronary arteries. In such prior art devices, the PZT transducer at the tip of the catheter is connected to appropriate instrumentation by electrical wires, which inherently act as antennas which receive radio frequency interference which is likely to be present in a catheterization laboratory. This RF interference is undesirably coupled to the PZT by introducing noise in the circuitry and also further increasing the risk of fibrillation. Furthermore, for sterility, the catheter must be disposable; with such a prior art device, disposing of the catheter necessitates disposing of the transducer, resulting in excessive cost.

In intravascular measurements, this system can measure the blood velocity, the flow rate at the proximal end of the coronary arteries, and in some cases it will provide an indication of an occluded blood vessel. The more successful attempts at imaging, use a PZT transducer with a rotating mirror, as described in "Laser Angioplasty's Ingeneous Hardware," *CARDIO* (August 1988); "Improved Monitoring of Laser Angioplasty with Laser Doppler Echocardiography," Bommer et al., *Journal of the American College of Cardiology*, (February 1988) 11:No. 2; and "Intra-arterial Ultrasonic Imaging for Recanalization by Spark Erosion," *Ultrasound in Medicine and Biology* (1988) 14:257–261.

To reach the quasi-distal end of the coronary arteries, the outer diameter of the catheter must not be larger than about 1.5 mm. Clearly there is an urgent need to greatly diminish the size of the Doppler catheter, especially if the ultimate objective is to explore the coronary vasculature. This objective becomes more important when the measurement of velocity or change of velocity is to be observed when a vasodilator is administered at the distal end of the catheter. Consequently, the PZT transducers used in the prior art had to be extremely small.

It has been shown by C. K. Jen, in "Similarities and Differences between Acoustics and Fiber Optics", IEEE Ultrasonics Symposium 1985, that conventional multimode "optical fibers" can also propagate acoustic longitudinal and shear pulses, and provide round trip acoustical transmission.

It is also well documented in the literature that similar optical fibers when excited by laser energy can utilize optical fluorescence techniques to monitor the concentration of blood gases like oxygen and carbon dioxide. These techniques are described in "Optical Fluorescence and its Application to an Intravascular Blood Gas Monitoring System" by John L. Gehrich, et al., in *IEEE Transactions on Biomedical Engineering*, Vol. BME-33, No. 2, February 1986.

It would be of significant advantage to the medical profession to have a combined probe that measures the blood flow velocity and monitors the $O_2$ and $CO_2$ concentration in the blood without using any active electrical components at the tip of the intravascular catheter. Such a probe would provide an invaluable and reliable tool for the patient care of 25 the critically ill, by enabling the intravascular surgeon to make quick and accurate diagnosis.

The basic principle involved in a monitoring sensor is the fluorescence of a dye which is specific to the gas being monitored. The wavelength of the emitted fluorescence is always lower than that of the input laser excitation and consequently a single optical fiber can be used to transmit the light through the fiber and receive the light emitted by the fluorescent dye. The intensity of the emitted light is inversely proportional to the gas concentration. In practical applications, the distal tip of the fiber is coated with the specific dye and it is protected by an external coating. Different dyes are available for monitoring the pH, $O_2$ and $CO_2$ concentrations in the blood.

SUMMARY OF THE INVENTION

In accordance with the teachings of this invention, a novel solution to the problems stated above is achieved by providing acoustic excitation at the catheter tip without the use of any electrically active devices. One or more acoustic fiber guides are used to carry certain modes of acoustic energy to the tip of the catheter. Using these fibers, reflected sound (Doppler sound) measurements are made in a blood environment without the risk to the patient associated with the use of an electrical transducer at the distal end of the catheter. Moreover, the fiber within the catheter does not pick up any radio frequency interference that might be present in a catheterization laboratory, because the signal transfer takes place via an acoustical fiber.

In accordance with the teachings of this invention, a Doppler probe is provided which is fitted at the end of a catheter that is less than approximately 1.00 mm OD, in which acoustical energy is generated outside of the patient and transported to the distal end of the catheter by an acoustic fiber. Due to this size reduction provided in accordance with the teachings of this invention, the Doppler probe of this invention is suitable for monitoring the blood flow in the coronary arteries. Using this invention wherein sound is transported to the catheter tip by an acoustic fiber, risk is reduced and the catheter is significantly less expensive, and therefore can be treated as disposable.

By the addition of optical fibers tipped with specific dyes and excited by optical energy of appropriate wavelength, the catheter tip system of this invention can also be utilized simultaneously as a combined (integral) optical blood ga and pH monitor using optical fluorescence and an acoustic Doppler velocity transducer.

The catheter tip system of this invention is suitable for use for Doppler signal analysis of the power spectrum, to determine the mean blood flow velocity and consequently the blood flow rate and cardiac output.

DETAILED DESCRIPTION

Doppler Flow Velocity Catheter Tip Transducer

Figure 3:
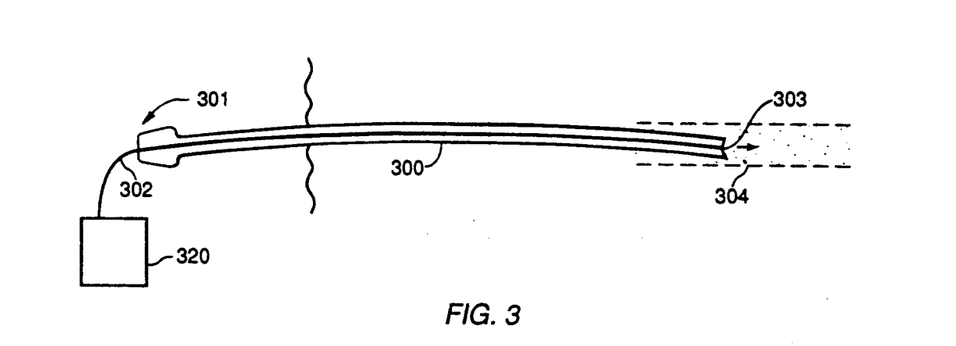
FIG. 3 depicts the use of a catheter for inserting within the bloodstream of a patient an acoustical sensor constructed in accordance with the teachings of this invention.

FIG. 3 depicts one embodiment of a catheter device constructed in accordance with the teachings of this invention. Catheter 300 is inserted into a patient such that its distal end 303 is located within blood vessel 304. Catheter 300 comprises a typical prior art catheter, for example, having a size number 3 French. Within catheter 300 is located an acoustical fiber 302, which in one embodiment comprises readily available optical fiber made of glass, for example. Optical fiber 302 exits catheter 300 at its proximal end 301, and is connected to means 320 for generating and coupling acoustical energy into fiber 302 and for detecting reflected acoustical energy from the red blood cells.

Means 320 comprises, for example, a surface acoustic wave device with curvilinear electrodes as described in copending U.S. patent application Ser. No. 07/352,517, filed May 16, 1989, on an invention of J. Fleming Dias entitled "Ultrasonic Catheter Guidance System", and assigned to Hewlett Packard Company. This device, when excited electrically, generates acoustic pulses that travel on the surface of a PZT substrate. These pulses converge at the center of the curvilinear electrodes where the fiber is affixed. The acoustic energy from the pulses is coupled into the proximal end of the fiber and propagates to the distal end. The reflected acoustic pulses also propagate through the fiber onto the surface of the PZT substrate and are converted into returning electrical pulses by the same curvilinear electrodes.

As is apparent from the embodiment of FIG. 3, a catheter device constructed in accordance with the teachings of this invention allows acoustical energy to be applied to the blood in blood vessel 304 and reflected acoustical energy to be sampled within blood vessel 304 without the need for electrical energy to e provided within blood vessel 304 or, indeed, within the patient at all. All of the electrical manipulation is done in circuitry 320, with all of the energy within the patient and blood vessel 304 being acoustical, rather than electrical, energy.

Figure 4A:
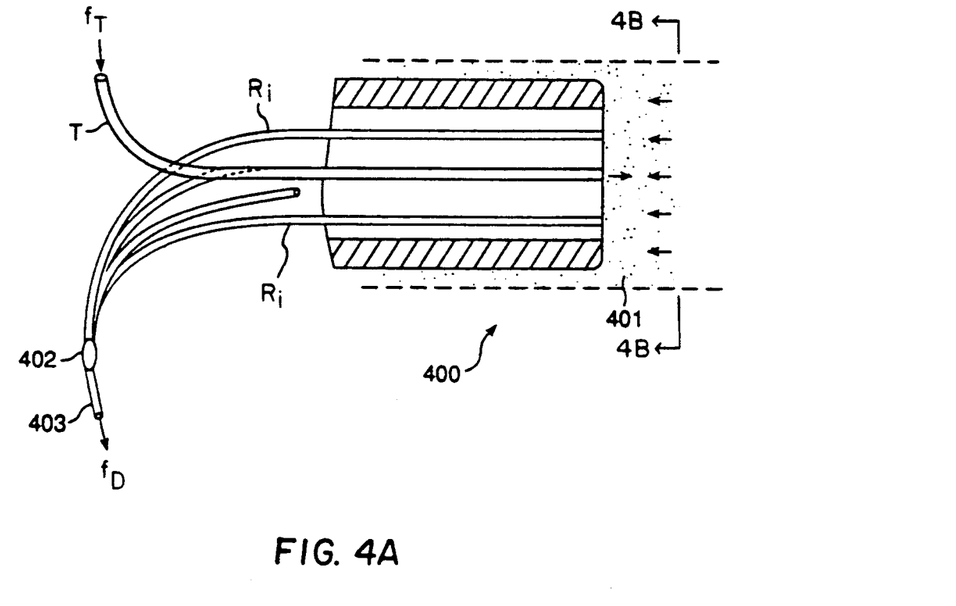
FIGS. 4A and 4B show a cross-sectional and end views of one embodiment of an acoustical sensor constructed in accordance with the teachings of this invention.
Figure 4B:
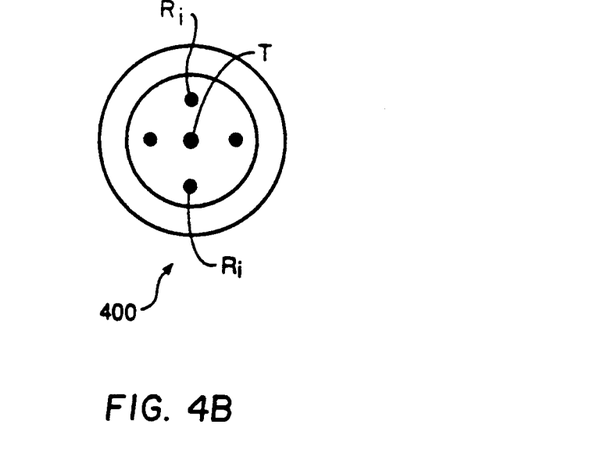

One embodiment of an acoustic fiber transducer constructed in accordance with the teachings of this invention is shown in the side and cross-sectional views of FIG. 4. Acoustical transducer 400 includes optical fiber guide "T", which is used as a transmitter of excitation ultrasound energy $f_T$ to insonify a volume of blood 401. A multiplicity of receiving fibers $R_i$ are used to receive the acoustic signal backscattered by the red blood corpuscles in the blood, which is shifted in frequency with respect to the excitation frequency. Receiving fibers $R_i$ are shown fused at point 402 using standard optical techniques to form a twisted acoustic coupler, such that a single optical fiber 403 is used to transmit the backscattered signal to detection equipment (as described above). This coupler adds all the received signals. The summed signal is Doppler shifted in frequency with respect to the excitation energy, and the net frequency shift is given by equation (1), and for clarity the constant delay through the fiber is not indicated.

$$f_D = 2f_T \frac{V\cos\theta}{C} ; \qquad (1)$$

where $f_D$ = doppler shift in frequency of the backscattered acoustic energy;
$f_T$ = frequency of the excitation energy;
C = velocity of sound in blood (1560 m/s);
$\theta$ = angle between the excitation energy beam and the velocity vector of the blood; and
V = velocity of blood flow.

In the case of intravascular Doppler measurements, the catheter is almost collinear with the blood flow and therefore $\theta$ is approximately 0, and thus $$f_D = \frac{2f_T V}{C} \quad (2)$$

The catheter tip Doppler device of this invention is useful in two modes of operation: A continuous wave mode, and a pulsed wave mode.

Figure 5:
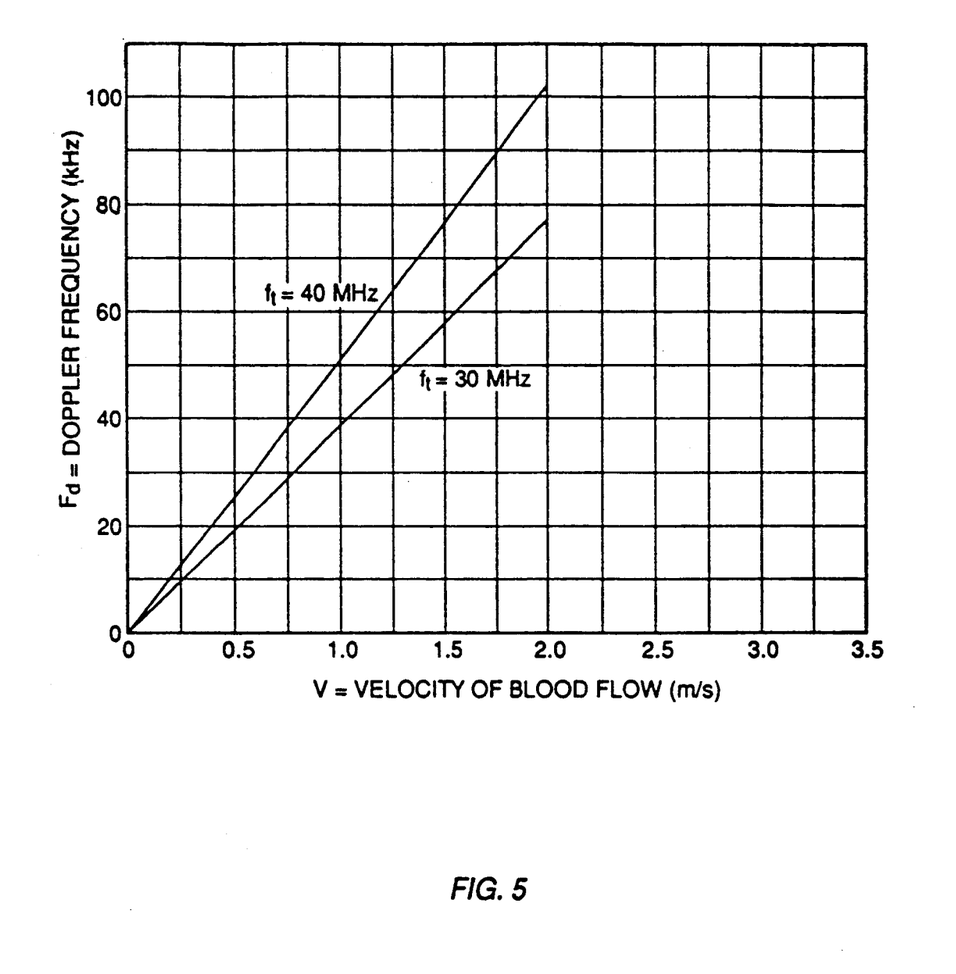
FIG. 5 is a graph depicting the relationship between doppler frequency and blood flow velocity, for two alternative excitation frequencies.

In a continuous wave mode, an estimate of blood velocity is obtained. In this mode, the backscattered sound comes from the full extent of the transmitted ultrasonic beam and therefore, while no range resolution is possible, there is no limit on the maximum velocity that can be measured. FIG. 5 depicts a graph showing velocity of blood flow versus Doppler shift frequency corresponding to excitation ultrasonic beams having frequency $f_T$ equal to 30 MHz and 40 MHz, respectively. Because of the ability to use much higher frequency sound in accordance with the teachings of this invention, it is now possible to measure very low blood flow velocities. For example, as shown in FIG. 5, using a 40 MHz acoustical excitation signal, blood flow velocity of approximately 0.25 m/s results in a 16 kHz Doppler shifted backscatter signal.

The frequency of 40 MHz was selected for several reasons:

(1) to obtain a higher signal to noise ratio;
(2) to measure a low blood flow velocity corresponding to a higher $f_D$;
(3) to prevent excessive attenuation of the acoustic signal through the blood; and
(4) to a certain extent, to achieve directivity in aiming.

Naturally, the teachings of this invention are equally applicable for use with excitation signals having a wide range of frequencies, since the fiber will propagate these frequencies with comparable efficiency.

In the pulsed wave mode, the measurement of the blood flow velocity is localized to a small volume in the blood. A sequence of pulses, consisting of a few cycles at frequency $f_T$ and at a suitable pulse repetition frequency, are transmitted by the distal end of the fiber into the blood. These acoustic pulses, as they propagate, reflect some energy back into the fibers. The frequency of the backscattered energy is Doppler shifted in frequency in direct proportion to the blood velocity V as shown in equation 1.

The location of the backscattered signal is determined by a variable delay range gate which defines the distance R of a range cell from the distal end face of the fiber. The length of the range cell is equal to the number of cycles in each pulse and the area is nominally proportional to the sectional area of the fiber. Consequently the volume of the range cells is the product of the two.

In the pulsed mode of operation there is a limit on the maximum velocity $V_m$ that can be measured before aliasing takes place. Aliasing is simply an ambiguity in determining the velocity and it is set by the sampling theorem which dictates that the pulse repetition frequency should be at least twice the Doppler shift in frequency.

Figure 6:
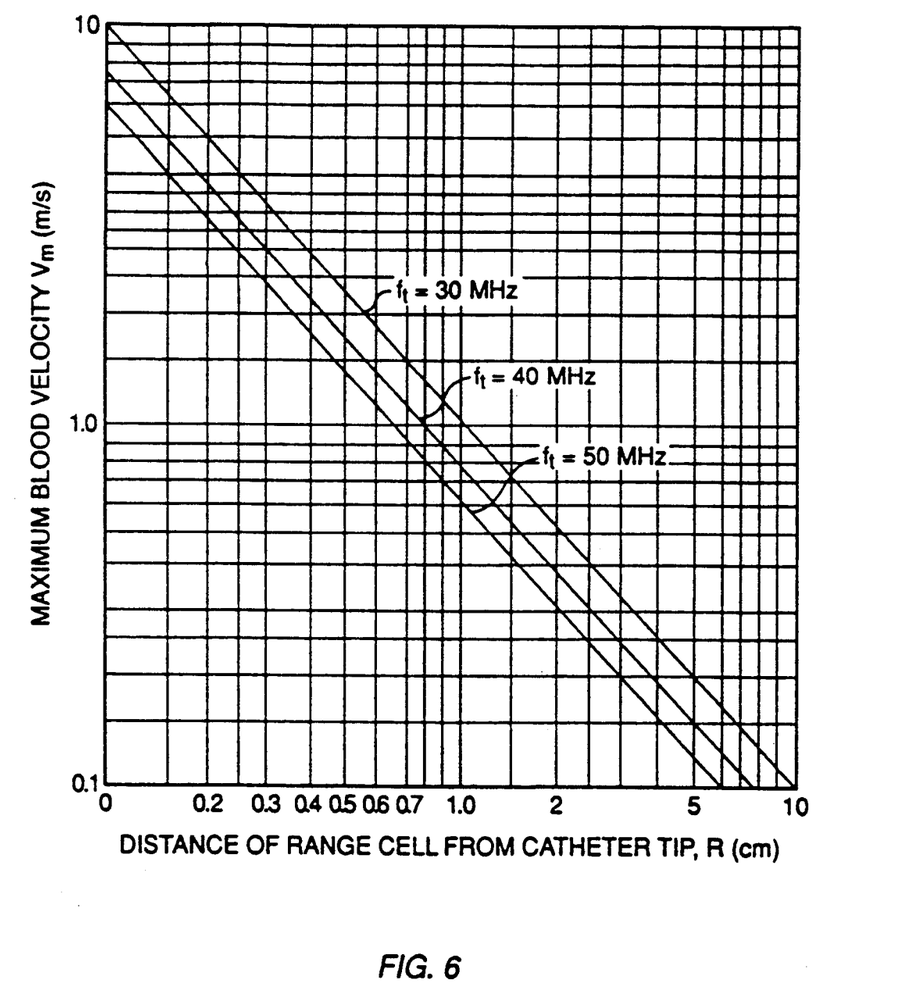
FIG. 6 is a graph depicting the relationship between blood velocity and the distance of the range cell from the catheter tip for three alternative excitation frequencies.

The length of the range cell from which the backscattered sound is received is determined by the pulse length. Hence, unlike an imaging situation where a short pulse length is necessary to obtain optimum in-line resolution, a longer pulse is required to increase the received signal. FIG. 6 shows a plot of velocity $V_m$ as a function of the distance R of the range cell from the catheter tip, related to pulse repetition frequency.

The maximum velocity $V_m$ of the blood that can be measured without frequency aliasing is given by $$V_m = \frac{C^2}{8f_T R} ; \quad (3)$$

where C = the speed of acoustical signals in blood (typically 1560 m/s)

Thus, in a 40 MHz acoustic fiber pulsed system, where the range cell is located 0.5 cm away from the tip (by adjusting the pulse repetition frequency), $$V_m = 1.5 \text{ m/s}.$$

This value of $V_m$ falls in the ranges given in "Doppler Ultrasound in Cardiology," *Physical Principles and Clinical Application*, Hatle, L. and Angelsen, B.

The pulse repetition frequency $f_s$ can be obtained from $$f_s = \frac{4f_T V_m}{C} \quad (4)$$

Thus, for the example given above, $f_s = 160$ kHz.

The corresponding Doppler Shift frequency $f_D$ given by equation (2) is 80.0 kHz. This Doppler Shift frequency is obtained, for example, by mixing the backscatter signal with a first local oscillator having a frequency equal to that of the excitation energy. For audible interpretation, The Doppler Shift signal is mixed with a second local oscillator having a frequency of approximately 70 to 75 kHz, resulting in an audible signal within the range of 5 to 10 kHz. If desired, of course, one or more local oscillators may be used to provide either an audible signal, or a detected signal within any desired frequency range.

Intravascular Doppler measurements using acoustic fiber (for example, multimode optical fibers) can be made at much higher frequencies compared to the noninvasive case. In the latter, these measurements are made at 2 to 5 MHz because of the attenuation in the body, i.e., 1dB/cm/MHz. For a 12 cm round trip, the total attenuation through the body is 60 dB at 5 MHz.

Using acoustic fibers, for a 1 cm round trip in blood, the total attenuation is about 20 dB. Adding the conversion and transmission loss through 1 meter of fiber of approximately 12 dB at 40 MHz yields a path loss of approximately 32 dB in accordance with the teachings of this invention, as compared with a path loss of approximately 60 dB utilizing prior art non-invasive techniques.

Furthermore, in accordance with the teachings of this invention, the coronary arteries are easily reached without any danger of any electrical potentials near the heart wall. The excitation sound is obtained by coupling the input end of optical fiber T (FIG. 4) to an acoustical transducer, such as the circular Interdigital Transducer (IDT) disclosed in the aforementioned copending application of Dias.

Of interest, the use of high frequencies with fibers has the advantageous result that backscattered signals per scatterer is increased and is proportional to $f^4_T$, as described by Hatle et al, cited above. Moreover, the receiver bandwidth can be reduced when the pulse length L is made longer and this in turn reduces the receiver noise N.

Hence, $$S \alpha F_T^4 V_{RC} \quad (5)$$

$$N \alpha 1/L \quad (6)$$

and therefore $$S/N \alpha = \frac{f_T^4 V_C}{1/L}$$

Thus $S/N = KF_T^4 V_{RC} L; \quad (8)$ where
S = signal from all scatterers;
N = receiver noise;
K = constant of proportionality; and
$V_{RC}$ = the volume of the range cell.

The S/N at higher frequencies (e.g. 40 MHz) provides a significant improvement over the S/N provided by prior art catheter tip PZT transducers operating at 10 MHz. Furthermore, acoustical transducer constructed in accordance with the teachings of this invention are significantly easier and cheaper to manufacture than prior art PZT transducers capable of operating at the same, or even lower, frequencies.

Combined Catheter Tip Blood Velocity Probe and Blood Gas/pH Monitor

Figure 7A:
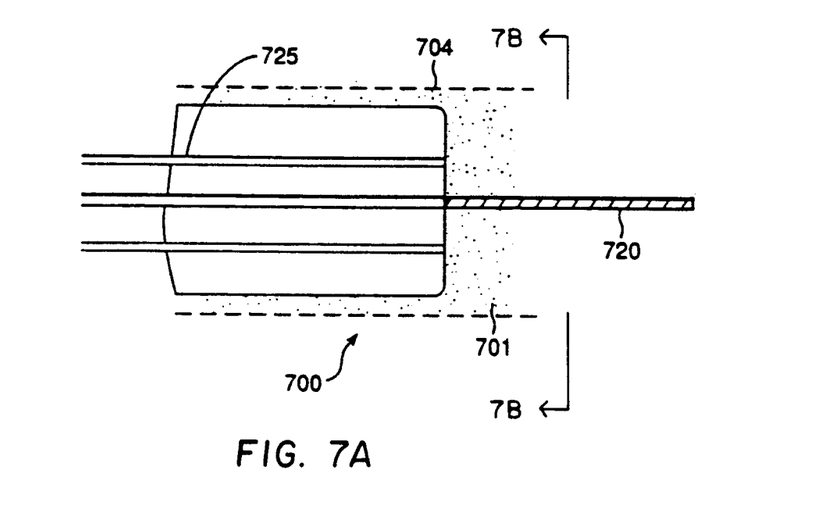
FIGS. 7A and 7B depict an alternative embodiment of a catheter constructed in accordance with the teachings of this invention including a guide wire, an acoustical sensor, and optical fibers used to measure blood gas concentrations by optical fluorescence.
Figure 7B:
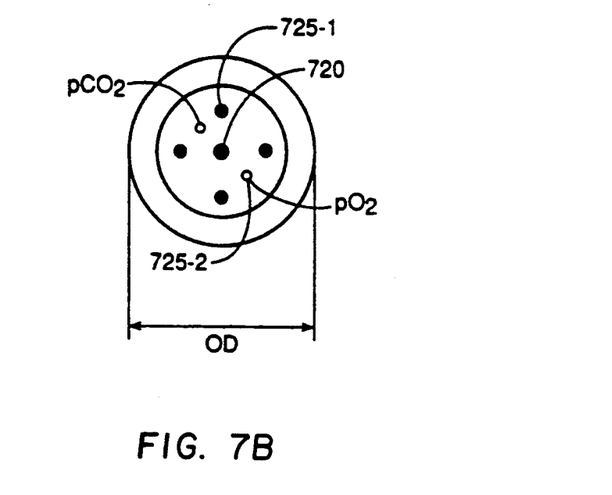

FIG. 7 depicts one embodiment of a combined catheter tip blood velocity probe and blood gas/pH monitor constructed in accordance with teachings of this invention. Transducer 700 includes a plurality of fibers 725, including for example, acoustical fiber 725-1 and optical fiber 725-2. Transducer 700 also includes guide wire 720 which is useful for guiding the transducer 700 within blood vessel 704. Acoustical fibers 725-1 serve as described above with regard to FIG. 4 to measure blood flow velocity within range cell 701. Integrally formed in transducer 700 are optical fibers 725-2 which are used, for example, to measure blood gas concentration in a well-known manner. For example, optical fibers 725-2 are coated on their tips with one or more specific fluorescent dyes. Excitation energy (for example from a laser) is then applied to the proximal ends of fibers 725-2, which is transmitted to the tips in order to excite the dyes. Fluorescent energy is coupled from the dyes to receiving instrumentation at the proximal ends of optical fibers 725-2. The amount of detected fluorescent energy with respect to the amount of excitation optical energy is indicative of the concentration of the blood gas (or pH) which has a specific affinity for the fluorescent dyes used.

If desired, the plurality of optical fibers 725-2 are used with various fluorescent dyes in order to provide a single transducer which measures a plurality of blood gas concentrations, as well as acoustically measuring blood velocity. Furthermore, if desired a single optical fiber is used to couple accoustical and optical energies from their respective sources to the sample being analyzed. Similarly, coupling the accoustical and optical energies from the sample to detection means can be achieved using the same optical fiber which is, if desired, the same optical fiber used to couple energies from the energy sources to the sample.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A system for measuring a physical parameter of fluid flow within a vessel comprising:
   a source of excitation acoustical energy located outside of said vessel;
   one or more acoustical fiber means for coupling said excitation acoustical energy to a selected location within said vessel for measuring said physical parameter; and
   one or more acoustical fiber means for coupling returning acoustical energy from said location within said vessel to a measurement device means for measuring flow within said vessel responsive to said returning acoustical energy.

2. A system as in claim 1 wherein said means for coupling are housed within a catheter device for insertion into said vessel.

3. A system as in claim 1 wherein said means for coupling returning acoustical energy comprises a plurality of acoustical return paths, and said means for coupling excitation acoustical energy is located centrally to said plurality of acoustical return paths.

4. A system as in claim 1 wherein said physical parameter is fluid flow rate and said returning acoustical energy is Doppler Shifted in frequency from said excitation acoustical energy.

5. A system as in claim 1 wherein said excitation acoustical energy comprises ultrasonic sound.

6. A system as in claim 1 which further comprises a wire guide for guiding said fibers within said vessel.

7. A system as in claim 1 which further comprises:
   a source of excitation optical energy located outside of said vessel;
   means for coupling said excitation optical energy from said source of excitation optical energy to said selected location; and
   means for coupling returning optical energy from said selected location to a measurement device for detecting gas concentration.

8. A system as in claim 7 wherein said means for coupling said acoustical energies and said means for coupling said optical energies are housed within a catheter device for insertion into said vessel.

9. A system as in claim 8 wherein said means for coupling said acoustical energies, comprise, one or more acoustical fibers and said means for coupling said optical energies comprise one or more optical fibers.

10. A system for detecting measuring fluid flow within a vessel comprising:

a source of excitation acoustical energy, located outside of said vessel;

a catheter means for insertion into said vessel to a selected location at which fluid flow is to be measured;

one or more acoustical fiber means for coupling via said catheter said excitation acoustical energy from said source to said selected location;

one or more acoustical fiber means for detecting fluid flow in response to returning energy produced as a function of said excitation energy and said fluid flow; and one or more acoustical fiber means for coupling returning energy from said selected location to said means for detecting fluid flow.

11. A system as in claim 10 wherein said means for coupling returning acoustical energy comprises a plurality of acoustical return paths, and said means for coupling excitation acoustical energy is located centrally to said plurality of acoustical return paths.

12. A system as in claim 10 wherein said returning acoustical energy is Doppler shifted from said excitation acoustical energy as a function of said fluid flow.

13. A system as in claim 10 wherein said excitation acoustical energy comprises ultrasonic sound.

14. A system as in claim 10 which further comprises:

a source of excitation optical energy located outside of said vessel;

means for coupling via said catheter said excitation optical energy from said source of excitation optical energy to said selected location;

means for detecting gas concentration in response to returning optical energy produced as a function of said excitation optical energy and said gas concentration; and means for coupling returning optical energy from said selected location to a measurement device for detecting gas concentration.

15. A system as in claim 14 wherein said means for coupling said excitation acoustical energy and said means for coupling said excitation optical energy comprises the same optical fiber.

16. A system as in claim 10 wherein said means for coupling said optical energies comprise one or more optical fibers.

* * * * *